United States Patent
Wu et al.

(10) Patent No.: US 8,101,379 B2
(45) Date of Patent: Jan. 24, 2012

(54) PREPARATION OF LOW BLEEDING ANTICOAGULANT FUSION PROTEIN AND ITS USE

(75) Inventors: Zuze Wu, Beijing (CN); Aiping Yu, Beijing (CN); Chuanling Zhang, Beijing (CN); Zhongxiong Tang, Beijing (CN)

(73) Assignees: Institute of Radiation Medicine Academy of Military Medical Science, Beijing (CN); Beijing Sanly Sci-Tech Develop Inc. Ltd., Beijing (CN)

( * ) Notice: Subject to any disclaimer, the term of this patent is extended or adjusted under 35 U.S.C. 154(b) by 0 days.

(21) Appl. No.: 12/519,309

(22) PCT Filed: Dec. 11, 2007

(86) PCT No.: PCT/CN2007/003526
§ 371 (c)(1),
(2), (4) Date: Dec. 22, 2009

(87) PCT Pub. No.: WO2008/071081
PCT Pub. Date: Jun. 19, 2008

(65) Prior Publication Data
US 2010/0113345 A1  May 6, 2010
US 2010/0234291 A2  Sep. 16, 2010

(30) Foreign Application Priority Data
Dec. 15, 2006 (CN) .......................... 2006 1 0165756

(51) Int. Cl.
*C12Q 1/68* (2006.01)
*C12P 21/06* (2006.01)
*C07K 1/00* (2006.01)

(52) U.S. Cl. .......................... 435/69.1; 530/350; 435/6

(58) Field of Classification Search .................. 530/350; 435/69.1, 6
See application file for complete search history.

(56) References Cited

U.S. PATENT DOCUMENTS
5,910,481 A * 6/1999 Voorberg .............. 514/14.9
6,156,888 A * 12/2000 Voorberg .............. 536/23.4

FOREIGN PATENT DOCUMENTS
CN    1896108 A     1/2007
EP    1 541 589     6/2005
WO    WO96/04004    2/1996

OTHER PUBLICATIONS

International Search Report as issued in PCT/CN2007/003526 on Mar. 27, 2008.
Jenny et al., "Critical Review of the Methods for Cleavage of Fusion Proteins with Thrombin and Factor Xa," Protein Expression and Purification, 31:1-11 (2003).
Niu et al., "Design and Functional Investigation of a Novel Anticoagulative Fusion Protein by Hirudin with a Recognizing Sequence of FXa," China Biotechnology, 26:36-39 (2006).
Saporito-Irwin et al., "Coagulation Factor XIa Cleaves the RHDS Sequence and Abolishes the Cell Adhesive Properties of the Amyloid β-Protein," J. Biol. Chem., 270-26265-26269 (1995).
Zhang et al., "Construction and functional evaluation of hirudin derivatives with low bleeding risk," Thrombosis and Haemostasis, 99:324-330 (2008).

* cited by examiner

*Primary Examiner* — Maryam Monshipouri
(74) *Attorney, Agent, or Firm* — Fish & Richardson P.C.

(57) ABSTRACT

Provided is an anticoagulant fusion protein comprising oligopeptide recognizable and cleavable by either factor XIa and factor Xa or thrombin and factor Xa. Also provided are the preparation method of the anticoagulant fusion protein and medicinal use thereof.

9 Claims, 2 Drawing Sheets

Nucleotide sequence of EH (SEQ ID NO:1)

GAACCTCGTATTACTTACACTGATTGTACAGAATCGGGTCAAA
ATTTGTGCCTCTGCGAGGGAAGCAATGTTTGCGGTAAAGGCAATAAGTGCATATT
GGGTTCTAATGGAAAGGGCAACCAATGTGTCACTGGCGAAGGTACACCGAAGCC
TGAAAGCCATAACAACGGCGATTTCGAAGAAATTCCAGAAGAATATTTACAATAA

Nucleotide sequence of GH (SEQ ID NO:2)

GGTGTTTACGCTCGTATTACTTACACTGATTGTACAGAATCGG
GTCAAAATTTGTGCCTCTGCGAGGGAAGCAATGTTTGCGGTAAAGGCAATAAGTG
CATATTGGGTTCTAATGGAAAGGGCAACCAATGTGTCACTGGCGAAGGTACACCG
AAGCCTGAAAGCCATAACAACGGCGATTTCGAAGAAATTCCAGAAGAATATTTAC
AATAA

Fig. 1

Amino acid sequence of EH (SEQ ID NO:3)

EPRITYTDCTESGQNLCLCEGSNVCGKGNKCILGSNGKGNQCVTGEGTP

KPESHNNGDFEEIPEEYLQ

Amino acid sequence of GH (SEQ ID NO:4)

GVYARITYTDCTESGQNLCLCEGSNVCGKGNKCILGSNGKGNQCVTGE

GTPKPESHNNGDFEEIPEEYLQ

Fig. 2

PREPARATION OF LOW BLEEDING ANTICOAGULANT FUSION PROTEIN AND ITS USE

This application is a 371 of PCT/CN07/03526, filed Dec. 11, 2007, which claims priority to Chinese patent application 200610165756.7, filed Dec. 16, 2006.

FIELD OF INVENTION

This invention belongs to the area of biotechnology, and relates to structure and preparation of a kind of anticoagulant substances with low hemorrhage and their application in prevention and treatment of thrombosis and thrombosis-related diseases. Particularly, this invention is related to a new substance obtained by linking an anticoagulant substance and an amino acid sequence being recognizable and cleavable by several blood coagulation factors, including thrombin, blood coagulation factor Xa (FXa) and XIa (FXIa) etc., and the preparation and pharmaceutical use of the same.

BACKGROUND OF INVENTION

Cardio-cerebrovascular diseases are number one killer threatening human health and life, and thrombosis is an important cause of many cardio-cerebrovascular diseases. Therefore, anticoagulants are important medicines used to prevent thrombosis. At present, heparin is an anticoagulant extensively used in clinical treatment. But one of its important shortcomings is to initiate thrombocytopenia. The newly developed Low-Molecular-Weight (LMW) heparin might decrease above risks, but can not thoroughly overcome its shortcomings.

People have focused more and more on above-mentioned shortcomings of prior anticoagulants. As an ideal anticoagulant, it should have the clear and definite anticoagulant effect, and should not cause the hemorrhagic side-effect in the case of systemic administration, so as to increase the clinical safety.

For this purpose, the key point of guiding principles for the present invention is that the anticoagulant function should be conditionally and specifically activated. That is, this kind of material normally has no anticoagulant activity, and only when the coagulation system is activated, and thrombus is possible to form or the thrombus formed, then this kind of anticoagulant locally display their anticoagulant activities. The local anticoagulant activity around the developing or developed thrombus forms a microenviroment to prevent thrombosis or the continued growing of the thrombus, even to dissolve the formed minute thrombus so as to attain the prophylactic/therapeutic purposes. Therefore, this invention would overcome the risk of systemic hemorrhage which often happens with administration of anticoagulant agents, such as heparin, hirudin etc.

For example, hirudin is a single chain polypeptide consisting of 65-66 amino acid residues, whose amino terminus can bind with the catalytic active site of thrombin, and possesses anticoagulant activity, and the binding of its C-terminus with the recognition site of thrombin substrate shows a very strong specific affinity to thrombin. This study designed a measure to block the amino-terminus of hirudin so as to diminish hirudin's anticoagulant activity temporarily. When the in vivo coagulation system is activated and thrombus formed, the special biochemical changes incited by thrombosis make the amino terminal-blocked hirudin recovered to the original form of hirudin displaying the specific anticoagulation effect at the location of potential or occurred thrombosis, thereby the systemic hemorrhagic side effect could be decreased. Therefore, this is a new type of safe and effective anticoagulant agent.

Under guidance of the above-mentioned inventive idea, hirudin was modified in this study. Hirudin first was linked by its amino-terminal with an oligopeptide recognizable and cleavable by thrombin, which is named as TH, or with an oligopeptide recognizable and cleavable by blood coagulation factor Xa, which is named as FH, so that once the coagulation system was activated, the anticoagulant activity of hirudin derivatives could be released and play the anticoagulant and antithrombotic roles, while the hemorrhagic side-effect would be also decreased. The results indicated that the modified hirudin was functional, but the effectiveness was not still high enough. Then, we developed our idea and considered that the hirudin might be modified by linking with an oligopeptide which can be recognized and cleaved by several blood coagulation factors or other factors. We hoped that the effectiveness could be enhanced by the above-mentioned modification to the extent of applicability to clinical practice. At present, however, on the basis of the related references, we can not infer if these oligopeptides can be recognized and cleaved by the corresponding blood coagulation factors in high efficiency. Two related proteins were prepared in our laboratory as follows: (1) hirudin was linked at its amino-terminal with the oligopeptide being recognizable and cleavable by both thrombin and coagulation factor Xa, this hirudin derivative being named as GH; (2) hirudin was linked at its amino-terminal with the oligopeptide being recognizable and cleavable by both coagulation factors XIa and Xa, this hirudin derivative being named as EH.

The research results indicated that these two derivatives of hirudin normally had no anticoagulation activity whether in vitro or in vivo, and could effectively release anticoagulation activity of hirudin locally under coacting of the above mentioned blood coagulation factors once coagulation system being activated, blood coagulation factors and play both roles of anticoagulation and antithrombosis. Certainly, There was no anticoagulation activity in the site of the body where thrombosis was absent, and thus their systemic hemorrhagic side-effect was also notably decreased. Therefore, unlike anticoagulant, such as hirudin and heparin, they are a kind of safe, effective anticoagulant and antithrombotic agents. As a result, this kind of anticoagulant agents with the characteristics of low hemorrhage is of importance to the application in prevention and/or treatment of thrombosis.

PURPOSE OF INVENTION

This invention is aimed at providing a kind of substance which has no anticoagulant activity itself and can release its anticoagulation activity around the site of thrombosis when thrombosis tends to occur or is occurring for prevention and/or treatment of thrombosis.

DISCLOSURE OF THE INVENTION

It is discovered in this invention that the anticoagulation activity of the anticoagulation substance could be blocked by linking the anticoagulation substance with a sequence recognizable by both coagulation factor XIa and Xa, or a sequence recognizable by both thrombin and coagulation factor Xa, and the new anticoagulation substance is cleavable at certain conditions. The derivatized anticoagulation substances possess the following characteristics: after blocked by a sequence recognizable by the above-mentioned two blood coagulation factors, the anticoagulation substance, such as hirudin, has no anticoagulation activity both in vitro and in non-thrombotic site of blood system, thus avoiding or decreasing the side-effects of systemic hemorrhage caused by anticoagulation substances, such as hirudin; the derivatized anticoagulation substances can locally release free anticoagulant substances under the action of blood coagulation factors specifically present in the site of thrombosis only when the thrombosis occurs, thus displays a prophylactic and/or therapeutic effects against thrombosis, and therefore significantly decreases the side-effect of systemic hemorrhage. Furthermore, the new anticoagulation substance, such as the amino-terminus of hirudin, blocked with a two coagulation factors-recognized sequence, can be cleaved by two coagulation factors together, the effectiveness of which is greatly superior to that of the block of anticoagulation substance by a one coagulation factor-recognized sequence. The discovery of this invention based on the above-mentioned characteristics has been completed at present.

Therefore, on the one hand, this invention is related to an anticoagulation substance which comprises an oligopeptide recognizable and cleavable by coagulation factors XIa and Xa together, or an oligopeptide recognizable and cleavable by thrombin and coagulation factor Xa together.

This invention, on the other hand, is related to a method for preparation of an anticoagulation substance comprising an oligopeptide recognizable and cleavable by coagulation factors XIa and Xa together, or an oligopeptide recognizable and cleavable by thrombin and coagulation factor Xa together, which comprises ligating a gene encoding anticoagulation protein with an base sequence corresponding to the sequence recognizable and cleavable by coagulation factors XIa and Xa together, or to the sequence recognizable and cleavable by thrombin and coagulation factor Xa together, then inserting the recombinant gene into a suitable expression vector, such as pBV220, pPIC9, and pPIC9K etc, and expressing the recombinant vector containing the gene of interest in appropriate host cells, such as *Escherichia coli*, yeast or animal cell systems, so as to obtain the new anticoagulation substance.

In further aspect, this invention is related to a pharmaceutical composition comprising the above-mentioned new anticoagulation substance and a pharmaceutically acceptable carrier or excipient.

According to the present invention, the term "anticoagulant substance" or "anticoagulation substance" indicates a substance against blood coagulation, such as hirudin, antithrombin III, snake venom etc. or their mutants; or the other substances with anticoagulation activity, preferably hirudin or its mutants.

According to the present invention, the terms "linked peptide recognizable by coagulation factors XIa and Xa together or linked peptide recognizable by thrombin and coagulation factor Xa together" or "oligopeptide recognizable by coagulation factors XIa and Xa together, or oligopeptide recognizable by thrombin and coagulation factor Xa together" are used to indicate the tripeptide EPR (GluProArg) or a peptide fragment containing EPR, or pentapeptide GVYAR (GlyValTyrAlaArg) or the peptide fragment containing GVYAR.

According to the present invention, the anticoagulation substance comprising an oligopeptide recognizable and cleavable by coagulation factors XIa and Xa together, or an oligopeptide recognizable and cleavable by thrombin and coagulation factor Xa together is preferably linked with EPR or GVYAR at the amino-terminal of hirudin.

According to the present invention, the anticoagulation substance comprising the oligopeptide recognizable and cleavable by coagulation factors XIa and Xa together, or the oligopeptide recognizable and cleavable by thrombin and coagulation factor Xa together may be expressed in appropriate host systems, preferably expressed in *E. coli* or yeast.

BRIEF DESCRIPTION OF THE FIGURES

FIG. 1 shows nucleotide sequences of EH and GH.
FIG. 2 shows amino acid sequences of EH and GH.
The following examples further illustrate this invention, but do not mean any limitation on this invention.

EXAMPLES

Preparation of EPR-HV2 (EH) and GVYAR-HV2 (GH), their Function in Prevention and/or Treatment of Thrombosis I. Preparation of EH and GH Protein Through PCR, a restriction site XhoI and a base sequence encoding the EPR sequence co-recognizable by coagulation factors XIa and Xa or the GVYAR sequence co-recognizable by thrombin and coagulation factor Xa were introduced at upstream of hirudin (HV2) gene, and a restriction site EcoRI was introduced at downstream of the gene. This gene was incorporated into pPIC9 plasmid that was digested by the same enzymes, thus recombinant plasmids pPIC-EH and pPIC9-GH were obtained. pPIC-EH and pPIC9-GH were digested with BamHI and SalI, and ligated to plasmid pPIC9K that was digested by the same enzymes, then pPIC9K-EH and pPIC9K-GH were obtained. The two recombinant plasmids were introduced into the yeast genome by electrotransformation and subjected to induction of expression by methanol. The expressed products were isolated and purified to get the proteins of interest of EH and GH.

II. Biological Activity of EH and GH

1. Analysis of Activities In Vitro

EH, GH, FH and TH were cleaved respectively by thrombin, FXa and FXIa, then the activities of anticoagulation were assayed by fibrin-clot method. The results were listed in Table 1.

TABLE 1

Analyses of anticoagulation activity of EH, GH, FH and TH before and after cleavage by thrombin, FXa and FXIa

| | group | | | | | | | | | | | |
|---|---|---|---|---|---|---|---|---|---|---|---|---|
| | GH | | | FH | | | TH | | | EH | | |
| | 0 h | 3 h | 6 h | 0 h | 3 h | 6 h | 0 h | 3 h | 6 h | 0 h | 3 h | 6 h |
| thrombin | 0 | 2 | 8 | 0 | 2 | 8 | 0 | 0 | 0 | 0 | 0 | 0 |
| FXa | 0 | 64 | 128 | 0 | 64 | 128 | 0 | 32 | 64 | 0 | 64 | 128 |
| FXIa | 0 | 0 | 0 | 0 | 0 | 0 | 0 | 0 | 64 | 0 | 256 | 512 |

It was shown in Table 1 that GH can be recognizable and cleavable by two blood coagulation factors of FXIa and FXa respectively, EH can be recognizable and cleavable by two blood coagulation factors of thrombin and FXa respectively, while FH only by FXa and TH only by thrombin.

2. Analysis of Antithrombosis and Hemorrhagic Side-Effects of GH and EH (1) Analyses of GH, EH, FH and TH antithrombotic and hemorrhagic side-effects in rat carotid artery thrombosis model, and the results were listed in table 2 and 3.

TABLE 2

Influence of GH, EH, FH and TH on time needed for thrombogenesis in rat carotid artery

| | group | | | |
|---|---|---|---|---|
| | NS | HV2 | EH | |
| | | 2 mg/kg | 2 mg/kg | 4 mg/kg |
| Time needed for thrombogenesis (s) | 779.30 ± 193.47 | 1117.00 ± 243.95## | 964.10 ± 179.68# | 1083.90 ± 227.10## |

| | group | | | |
|---|---|---|---|---|
| | NS | HV2 | GH | |
| | | 2 mg/kg | 2 mg/kg | 4 mg/kg |
| Time needed for thrombogenesis (s) | 779.30 ± 193.47 | 1117.00 ± 243.95## | 918.10 ± 204.16 | 1006.7 ± 227.37# |

| | group | | | |
|---|---|---|---|---|
| | NS | HV2 | FH | |
| | | 2 mg/kg | 2 mg/kg | 4 mg/kg |
| Time needed for thrombogenesis (s) | 779.30 ± 193.47 | 1117.00 ± 243.95## | 988.10 ± 231.16 | 1096.0 ± 255.9# |

| | group | | | |
|---|---|---|---|---|
| | NS | HV2 | TH | |
| | | 2 mg/kg | 2 mg/kg | 4 mg/kg |
| Time needed for thrombogenesis (s) | 779.30 ± 193.47 | 1117.00 ± 243.95## | 881.50 ± 145.18 | 927.80 ± 152.84# |

Each group was consisted of 10 animals and the results were shown as $\bar{X}$ ± SD; HV2: hirudin; NS: normal saline.

$p < 0.05$,

$p < 0.01$, compared to NS group

TABLE 3

Influence of EH, GH, FH and TH on plasma TT
levels in rat carotid artery thrombosis model

| | group | | | |
|---|---|---|---|---|
| | HV2 | | EH | |
| | NS | 2 mg/kg | 2 mg/kg | 4 mg/kg |
| % of TT changes | 100 ± 0 | 1005.62 ± 361.28** | 108.41 ± 12.95 | 121.81 ± 13.68** |

| | group | | | |
|---|---|---|---|---|
| | HV2 | | GH | |
| | NS | 2 mg/kg | 2 mg/kg | 4 mg/kg |
| % of TT changes | 100 ± 0 | 1005.62 ± 361.28** | 104.35 ± 17.21 | 114.94 ± 19.82** |

| | group | | | |
|---|---|---|---|---|
| | HV2 | | FH | |
| | NS | 2 mg/kg | 2 mg/kg | 4 mg/kg |
| % of TT changes | 100 ± 0 | 1005.62 ± 361.28** | 119.31 ± 16.32 | 149.66 ± 50.84* |

| | group | | | |
|---|---|---|---|---|
| | HV2 | | TH | |
| | NS | 2 mg/kg | 2 mg/kg | 4 mg/kg |
| % of TT changes | 100 ± 0 | 1005.62 ± 361.28** | 117.57 ± 14.82 | 141.03 ± 54.31* |

Each group was consisted of 10 animals and the result of NS group was shown as 100%, and the results of other groups were expressed as the percentage changes of each group compared with NS group. The results were expressed as $\bar{X}$ ± SD. HV2: hirudin, NS: normal saline.

*$P < 0.05$,

**$P < 0.01$ compared with NS group;

$P < 0.01$, HV2 group compared with each of the other groups.

(2) The hemorrhagic side-effects of GH, EH, TH and FH in hemorrhagic model of tail-cut mouse were analyzed, and the results were listed in Table 4.

TABLE 4

Influence of EH, GH, FH and TH on bleeding time of tail-cut mouse

| | | group | | |
|---|---|---|---|---|
| | | HV2 | EH | |
| | NS | 1.5 mg/kg | 1.5 mg/kg | 6 mg/kg |
| Bleeding time (s) | 156.14 ± 125.08 | 1532.5 ± 420.74 | 203.89 ± 97.41 | 338.77 ± 169.08* |

| | | group | | |
|---|---|---|---|---|
| | | HV2 | GH | |
| | NS | 1.5 mg/kg | 1.5 mg/kg | 6 mg/kg |
| Bleeding time (s) | 156.14 ± 125.08 | 1532.5 ± 420.74 | 165.46 ± 142.42 | 304 ± 178.99*# |

| | | group | | |
|---|---|---|---|---|
| | | HV2 | FH | |
| | NS | 1.5 mg/kg | 1.5 mg/kg | 6.0 mg/kg |
| Bleeding time (s) | 156.14 ± 125.08 | 1532.5 ± 420.74 | 264.08 ± 209.74 | 569.14 ± 430.1* |

| | | group | | |
|---|---|---|---|---|
| | | HV2 | TH | |
| | NS | 1.5 mg/kg | 1.5 mg/kg | 6 mg/kg |
| Bleeding time (s) | 156.14 ± 125.08 | 1532.5 ± 420.74 | 241.42 ± 194.49 | 397.31 ± 286.12* |

Each group was consisted of 15 animals and the result was expressed as $\overline{X}$ ± SD.
*$P < 0.05$, compared with NS group;
$P < 0.01$, HV2 group compared with each of the other groups;
$P < 0.05$, GH group compared with FH and TH group.

It was observed from table 2 that the time needed for thrombogenesis was prolonged in a dose-dependent manner by EH, GH, FH and TH in rat carotid artery thrombosis model, which indicated that each of the four derivatives of hirudin had the ability to function against arterial thrombosis, with efficacies substantially similar to each other. However, the hemorrhagic side-effects were quite different from each other. From table 3 and 4, it was shown that the influence of GH, EH, FH and TH on hemorrhagic indexes is less than that of HV2, indicating a higher safety of them than that of HV2. However, GH and EH had a much less effect on bleeding index than that of FH and TH, and particularly GH had a significantly shorter bleeding time than that of FH and TH group, indicating that GH and EH are significantly better than FH or TH in decreasing hemorrhagic side-effect.

The invention claimed is:

1. An anticoagulant protein comprising hirudin, antithrombin III, or snake venom, linked to an oligopeptide recognizable and cleavable by two blood coagulation factors together.

2. The anticoagulant protein according to claim 1, comprising hirudin.

3. The anticoagulant protein comprising an oligopeptide recognizable and cleavable by two blood coagulation factors together according to claim 1, wherein the blood coagulation factor is thrombin, coagulation factor Xa, or coagulation factor XIa.

4. An anticoagulant protein comprising an oligopeptide recognizable and cleavable by two blood coagulation factors together according to claim 1, wherein the oligopeptide is an amino acid sequence recognizable by coagulation factor XIa and coagulation factor Xa together, or an amino acid sequence recognizable by thrombin and coagulation factor Xa together, or an oligopeptide comprising an amino acid sequence recognizable by coagulation factor XIa and coagulation factor Xa together or an oligopeptide comprising an amino acid sequence recognizable by thrombin and coagulation factor Xa together.

5. The amino acid sequence recognizable and cleavable by coagulation factor XIa and coagulation factor Xa together or the amino acid sequence recognizable and cleavable by thrombin and coagulation factor Xa together according to claim 4, which is an amino acid sequence EPR or a peptide fragment comprising EPR recognizable and cleavable by coagulation factor XIa and coagulation factor Xa together, or an amino acid sequence GVYAR or a peptide fragment comprising GVYAR recognizable and cleavable by thrombin and coagulation factor Xa together.

6. The anticoagulant protein comprising an oligopeptide recognizable and cleavable by two blood coagulation factors together according to claim 1, which includes the anticoagulant protein EH (SEQ ID NO:1) with EPR linked to N-terminus of hirudin.

7. A method for preparation of an anticoagulant protein comprising hirudin, antithrombin III, or snake venom, linked to an oligopeptide recognizable and cleavable by coagulation factor XIa and coagulation factor Xa together or comprising an oligopeptide recognizable and cleavable by thrombin and coagulation factor Xa together, which comprises introducing a nucleotide sequence encoding EPR or GVYAR into upstream of a gene encoding the anticoagulant protein, then expressing the gene.

8. A pharmaceutical composition comprising an anticoagulant protein comprising hirudin, antithrombin III, or snake venom, linked to an oligopeptide recognizable and cleavable by coagulation factor XIa and coagulation factor Xa together or an oligopeptide recognizable and cleavable by thrombin and coagulation factor Xa together, and a pharmaceutically acceptable carrier or excipient.

9. The anticoagulant protein comprising an oligopeptide recognizable and cleavable by two blood coagulation factors together according to claim 1, which includes the anticoagulant protein GH (SEQ ID NO:2) with GVYAR linked to N-terminus of hirudin.

* * * * *

UNITED STATES PATENT AND TRADEMARK OFFICE
CERTIFICATE OF CORRECTION

Page 1 of 1

PATENT NO. : 8,101,379 B2
APPLICATION NO. : 12/519309
DATED : January 24, 2012
INVENTOR(S) : Zuze Wu et al.

It is certified that error appears in the above-identified patent and that said Letters Patent is hereby corrected as shown below:

Title page, Item [73] (Assignee), line 1, delete "Medicine" and insert -- Medicine, --

Title page, Item [73] (Assignee), line 2, delete "Science," and insert -- Sciences, PLA --

Signed and Sealed this
Twenty-seventh Day of November, 2012

David J. Kappos
*Director of the United States Patent and Trademark Office*

```
                        SEQUENCE LISTING

<160> NUMBER OF SEQ ID NOS: 6

<210> SEQ ID NO 1
<211> LENGTH: 207
<212> TYPE: DNA
<213> ORGANISM: Artificial Sequence
<220> FEATURE:
<223> OTHER INFORMATION: Nucleotide Sequence of EH

<400> SEQUENCE: 1
gaacctcgta ttacttacac tgattgtaca gaatcgggtc aaaatttgtg cctctgcgag      60
ggaagcaatg tttgcggtaa aggcaataag tgcatattgg gttctaatgg aaagggcaac     120
caatgtgtca ctggcgaagg tacaccgaag cctgaaagcc ataacaacgg cgatttcgaa     180
gaaattccag aagaatattt acaataa                                         207
```

```
<210> SEQ ID NO 2
<211> LENGTH: 213
<212> TYPE: DNA
<213> ORGANISM: Artificial Sequence
<220> FEATURE:
<223> OTHER INFORMATION: Nucleotide Sequence of GH

<400> SEQUENCE: 2
ggtgtttacg ctcgtattac ttacactgat tgtacagaat cgggtcaaaa tttgtgcctc    60
tgcgagggaa gcaatgtttg cggtaaaggc aataagtgca tattgggttc taatggaaag   120
ggcaaccaat gtgtcactgg cgaaggtaca ccgaagcctg aaagccataa caacggcgat   180
ttcgaagaaa ttccagaaga atatttacaa taa                                213

<210> SEQ ID NO 3
<211> LENGTH: 68
<212> TYPE: PRT
<213> ORGANISM: Artificial Sequence
<220> FEATURE:
<223> OTHER INFORMATION: Nucleotide Sequence of EH

<400> SEQUENCE: 3

Glu Pro Arg Ile Thr Tyr Thr Asp Cys Thr Glu Ser Gly Gln Asn Leu
 1               5                  10                  15

Cys Leu Cys Glu Gly Ser Asn Val Cys Gly Lys Gly Asn Lys Cys Ile
             20                  25                  30

Leu Gly Ser Asn Gly Lys Gly Asn Gln Cys Val Thr Gly Glu Gly Thr
         35                  40                  45

Pro Lys Pro Glu Ser His Asn Asn Gly Asp Phe Glu Glu Ile Pro Glu
     50                  55                  60

Glu Tyr Leu Gln
 65

<210> SEQ ID NO 4
<211> LENGTH: 70
<212> TYPE: PRT
<213> ORGANISM: Artificial Sequence
<220> FEATURE:
<223> OTHER INFORMATION: Nucleotide Sequence of GH

<400> SEQUENCE: 4

Gly Val Tyr Ala Arg Ile Thr Tyr Thr Asp Cys Thr Glu Ser Gly Gln
 1               5                  10                  15

Asn Leu Cys Leu Cys Glu Gly Ser Asn Val Cys Gly Lys Gly Asn Lys
             20                  25                  30

Cys Ile Leu Gly Ser Asn Gly Lys Gly Asn Gln Cys Val Thr Gly Glu
         35                  40                  45

Gly Thr Pro Lys Pro Glu Ser His Asn Asn Gly Asp Phe Glu Glu Ile
     50                  55                  60

Pro Glu Glu Tyr Leu Gln
 65                  70

<210> SEQ ID NO 5
<211> LENGTH: 3
<212> TYPE: PRT
<213> ORGANISM: Artificial Sequence
<220> FEATURE:
<223> OTHER INFORMATION: Peptide Fragment Containing EPR

<400> SEQUENCE: 5

Glu Pro Arg
 1
```

```
<210> SEQ ID NO 6
<211> LENGTH: 5
<212> TYPE: PRT
<213> ORGANISM: Artificial Sequence
<220> FEATURE:
<223> OTHER INFORMATION: Peptide Fragment Containing GVYAR

<400> SEQUENCE: 6

Gly Val Tyr Ala Arg
 1               5
```